US008232317B2

(12) United States Patent
Gan et al.

(10) Patent No.: US 8,232,317 B2
(45) Date of Patent: Jul. 31, 2012

(54) METHOD FOR INCREASING HAIR GROWTH

(75) Inventors: David C. Gan, Huntington Sta., NY (US); Geoffrey Hawkins, Penn Valley, PA (US); Thomas Mammone, Farmingdale, NY (US); Richard Presti, East Meadow, NY (US); Rose Marie Sparacio, Manorville, NY (US)

(73) Assignee: E-L Management Corp., New York, NY (US)

( * ) Notice: Subject to any disclaimer, the term of this patent is extended or adjusted under 35 U.S.C. 154(b) by 75 days.

(21) Appl. No.: 12/570,055

(22) Filed: Sep. 30, 2009

(65) Prior Publication Data
US 2010/0022651 A1 Jan. 28, 2010

Related U.S. Application Data

(63) Continuation of application No. 10/786,847, filed on Feb. 25, 2004, now Pat. No. 7,790,768.

(60) Provisional application No. 60/495,915, filed on Aug. 18, 2003, provisional application No. 60/451,193, filed on Feb. 28, 2003.

(51) Int. Cl.
*A61Q 5/00* (2006.01)
(52) U.S. Cl. ........................................ 514/564; 424/70.1
(58) Field of Classification Search ........................ None
See application file for complete search history.

(56) References Cited

U.S. PATENT DOCUMENTS

| | | | |
|---|---|---|---|
| 5,053,230 A * | 10/1991 | Gazzani | 424/582 |
| 5,750,512 A | 5/1998 | Birkmayer | |
| 5,998,457 A | 12/1999 | Kaddurah-Daouk et al. | |
| 6,075,031 A | 6/2000 | Kaddurah-Daouk et al. | |
| 6,242,491 B1 | 6/2001 | Kaddurah-Daouk et al. | |
| 6,333,057 B1 * | 12/2001 | Crandall | 424/727 |
| 7,790,768 B2 * | 9/2010 | Gan et al. | 514/564 |
| 2004/0029969 A1 | 2/2004 | Blatt et al. | |
| 2004/0241197 A1 | 12/2004 | Biergiesser et al. | |

FOREIGN PATENT DOCUMENTS

| | | |
|---|---|---|
| DE | 10114561 | 9/2002 |
| DE | 10119608 | 10/2002 |
| EP | 0565010 | 10/1993 |
| EP | 0688555 | 12/1995 |
| EP | 0998907 | 5/2000 |
| EP | 1040815 A1 | 10/2000 |
| GB | 2084726 | 4/1982 |
| WO | WO02/11717 | 2/2002 |

OTHER PUBLICATIONS

PCT International Search Report; International Application No. PCT/US04/05765; Completion Date: Feb. 16, 2005; Date of Mailing: Apr. 1, 2005.
PCT Written Opinion of the International Searching Authority; International Application No. PCT/US04/05765; Mailing Date: Apr. 1, 2005.
Supplementary European Search Report; EP04714661.8; Completion Date: Dec. 14, 2007; Date of Mailing: Dec. 28, 2007.
Matthews, et al.; Neuroprotective Effects of Creatine and Cyclocreatine in Animal Models of Huntington's Disease; The Journal of Neuroscience; 18(1):156-163; 1998.
Shimaoka, et al.; Dermal papilla cells express hepatocyte growth factor; Journal of Dermatological Science; 7 (Suppl.); pp. S79-S83; 1994.
Supplmentary European Search Report from the Divisional EP Application No./Patent No. 09168182.5; Completion Date: Oct. 12, 2009; Mailing Date: Oct. 26, 2009.

* cited by examiner

*Primary Examiner* — Jyothsna Venkat
(74) *Attorney, Agent, or Firm* — Julie Blackburn

(57) ABSTRACT

The present invention provides a method for stimulating hair growth, which comprises applying a composition containing a combination of a creatine compound and carnitine. The composition may further comprise 5'-AMP and NADH. Such a composition is effective in stimulating cell proliferation in the hair bulb of hair plugs.

7 Claims, No Drawings

METHOD FOR INCREASING HAIR GROWTH

CROSS-REFERENCE TO RELATED APPLICATIONS

This is a continuation of U.S. patent application Ser. No. 10/786,847 filed on Feb. 25, 2004, now U.S. Pat. No. 7,790,768 which claims priority to U.S. Provisional Patent Application No. 60/495,915 filed on Aug. 18, 2003 and U.S. Provisional Patent Application No. 60/451,193 filed on Feb. 28, 2003.

FIELD OF THE INVENTION

The invention relates to the field of personal care. More specifically, the invention relates to methods for increasing hair growth and prevention of hair loss.

BACKGROUND OF THE INVENTION

The quest to find a safe, reliable methodology for treating and preventing baldness has been ongoing for many years. Although certainly not life-threatening, the loss of hair, in both men and women, causes significant distress to the afflicted individual, and can seriously affect the individual's self-esteem. The problems involved in finding a safe and effective treatment are many. First, the underlying cause of the hair loss is not always the same from individual to individual. Also, the process by which hair grows encompasses several phases and there are many contributory factors that can alter the normal vigorous growth of hair. The hair growth cycle is divided into three phases: an anagen phase, in which the hair is growing actively, with a very substantial level of cell proliferation occurring in the hair follicle; a catagen phase, when the follicle slows down its proliferative activity temporarily to permit hair development; and a telogen phase, in which the follicle simply stops growing and regresses, until the hair is shed, and a new anagen phase begins.

It is of course completely normal for the average person to lose many hairs on a daily basis, and therefore, this cycle is normally repeated continually throughout life, to replenish the hair that is lost. The cycle does slow down with age in all individuals, however with the normal hairs gradually being replaced by progressively finer hair (vellus hair), and the cycles becoming shorter. For individuals who suffer from abnormal hair loss, it is apparent that the normal cyclical process becomes disrupted in some fashion, whether it be through an abnormal acceleration or other alteration of the process; this eventually results in a more rapid shift to the telogen phase, which in turn gradually results in the production of more vellus hair and ultimately may result in baldness.

The causes of this shift to shorter cycles is still not completely understood. A large number of factors contribute to the pattern of hair growth, including, but not limited to, diet, drug exposure, and hormones. A variety of different types have been proposed over the years for treatment of hair loss; these treatments may attempt to counteract the effects of the harmful factors, such as hormones, or they may attempt to directly restimulate the activity in dormant follicles. Many of the agents that have been shown to be successful in renewing hair growth are synthetic pharmaceutical agents, such as minoxidil or procaine. While these materials are effective, they do have some disadvantages in that, as drugs, they may have undesired systemic effects, and/or they may have to be administered orally; in many cases, the treatments are largely targeted to androgenic alopecia, or male pattern baldness, and therefore may not be safe or effective for use by female candidates experiencing hair loss. The gold standard for hair growth enhancers is therefore a natural material that is not hormonal either in chemical nature or in target, that can be administered topically without concern to both males and females experiencing hair loss, and which preferably has a direct effect on stimulation of the hair follicle itself. Although a number of naturally occurring materials, such as saw palmetto, have been recommended for use in the promotion of hair growth, there has been no widespread commercial success or acceptance of any of the natural remedies for hair loss by both men and women. There thus continues to be a need for a method of treating hair loss that utilizes a non-hormonal naturally occurring material as its active component. The present invention now provides such a method.

SUMMARY OF THE INVENTION

The present invention relates to a method for stimulating proliferative activity in hair follicles which comprises applying to the hair follicle a follicle-stimulating effective amount of creatine or a creatine derivative. The invention also relates to a method for treating or preventing hair loss which comprises applying topically to the hair and/or scalp a follicle-stimulating effective amount of creatine, or a creatine derivative. The method of the invention thus utilizes a naturally occurring material, creatine, that is normally present in human cells, to increase the level of hair growth in hair follicles.

DETAILED DESCRIPTION OF THE INVENTION

The present inventors have observed, unexpectedly, that creatine, when applied to dermal papilla cells, is capable of producing a significant increase in the level of DNA synthesis of those cells (see Example 1). Dermal papilla cells are present in the hair follicle, and have been suggested to be involved in hair growth by modulating the activity of keratinocyte (matrix cells) proliferation and differentiation (Shimaoka et al., *J. Dermatol. Sci.* 7(Suppl): S79-S83, 1994) It was therefore attempted to determine in the increase in DNA synthesis could be translated into actual increase in hair growth. Again unexpectedly, the application of creatine, in amounts of as little as 1 mM, is capable of increasing actual hair length in hair plugs relative to untreated controls by statistically significant levels (see Example 2), thus confirming its efficacy in treating and preventing hair loss.

Creatine is a naturally-occurring material that is normally present in various mammalian tissues, such as the heart, skeletal muscle, brain and retina. It has previously found many therapeutic uses, for example, in the treatment of glucose metabolic disorders (U.S. Pat. No. 6,075,031); in the treatment of obesity (U.S. Pat. No. 5,998,457); and treatment of skin damage (U.S. Pat. No. 6,242,491). It has not previously, to Applicants' knowledge, been known for use in the promotion of hair growth. The creatine employed in the present invention can be naturally derived, i.e., isolated directly from biological material, or can be obtained synthetically or semi-synthetically. In addition to creatine per se, the method can also be employed using creatine derivatives or analogues. Examples of such materials include but are not limited to, creatine phosphate and cyclocreatine; other creatine analogues are also known and have been disclosed, for example, in U.S. Pat. No. 6,075,031, the contents of which are incorporated herein by reference. As used in the present context, the term "creatine compound(s)" refers to both creatine and creatine analogues that exhibit the same type of stimulatory activity. The follicle-stimulating effective amount employed in the present method is that amount that is capable of increasing the hair growth of a follicle at least 20% above the growth observed in an untreated follicle, preferably increasing at least 40%, more preferably at least 50%, and most preferably at least 80%.

The creatine compound is used in the form of a topical formulation for application to the hair and scalp. The composition of the formulation is not critical, and the vehicle may be any that is acceptable for topical application, particularly compositions adapted for application to hair or scalp. The formulation may be applied as a shampoo, a hair rinse, a conditioner, a pomade, a gel, or any other form that is normally used for treatment of hair. In a preferred embodiment, the composition is applied as a shampoo, conditioner or rinse. In practical terms, the "effective amount" used in a formulation will generally be from about 0.0001 to about 20%, preferably about 0.001 to about 10%, more preferably about 0.01 to about 10%, by weight of the total composition.

The compositions may contain one or more creatine compounds alone as active agent, or they may be combined with other active agents that also exhibit beneficial effects on the hair and scalp. Particular benefit to hair growth may be achieved with the combination of at least one additional energy enhancing actives, such as adenosine, ATP, ADP, AMP, oxaloacetic acid (oxaloacetate), NADH, NADPH, or carnitine, or its derivatives, such as acetyl carnitine or palmitoyl carnitine, each of which also may have a beneficial effect on the growth of hair. The overall amount of energy-inducing compounds used in the composition, including creatine, will be from about 0.0001 to about 10% by weight, preferably about 0.01 to about 5%. Particularly preferred is a combination of creatine with at least one of 5'-AMP, NADH and carnitine, and an extremely effective combination occurs with all four components in the composition.

The hair growth compositions of the invention may also optionally include other active components having a beneficial effect on hair growth. One type of additional active is a 5-alpha reductase inhibitor. Such compounds are known to assist in promotion of hair growth, and include, but are not limited to saw palmetto (*Serenoa*) extract, *Emblica officianalis* extract, Beta-glycyrrhetic acid, estradiol, estrone, progesterone, or azasteroids, such as finasteride or dutasteride. It is particularly preferred that the reductase inhibitor be naturally derived. A particularly preferred naturally derived inhibitor is a refined saw palmetto berry extract, commercially available as Viapure Sabal from Actives International, Ramsey, N.J. The amount of reductase inhibitor used will vary depending upon the identity and potency of the material, but will be in accordance with the known effective ranges for the material. The amount will generally be in the range of about 0.0001-10%, and for the preferred material, saw palmetto extract, this amount will preferably be from about 0.001 to about 2%.

The compositions of the invention can also be improved by the incorporation of one or more antiinflammatory agents. Examples of useful antiinflammatory materials include, but are not limited to, luteolin, amentoflavone, hoelen mushroom extract (*Poria cocos*), stearyl glycyrrhetinate and other antiinflammatory glycyrrhizic acid derivatives, manuka oil, emu oil, *echinacea*, chamomile (*matricaria* oil), *scuttelaria* extracts, *artemisia* extracts, gentian extract, soybean protein, calendula, cayenne, turmeric, white willow, sialyl sugars (e.g., 3' sialyl lactose) and the like. Total amounts of antiinflammatory agents in the formulation will ordinarily be in the range of from about 0.0001 to about 10%.

It may also be desirable to incorporate into the formulation a pigmentation enhancer, which, while not contributing directly to hair growth, will enhance the overall benefit of the product by darkening lighter, less noticeable hair, such as vellus hair. Examples of useful pigmentation enhancers are N-acetyl-L-tyrosine, tyrosine, forskolin, phenylalanine, L-DOPA, methylxanthine, or α-melanocyte stimulating hormone. The pigmentation enhancing agents will be used in an amount of about 0.0001 to about 10%.

Vasodilation enhancers are also an optional component of the formulation. Vasodilation has long been associated with an increase in hair growth, not only on the scalp, but also on any other area of the skin where hair grows. Thus, use of one or more vasodilation agents can supplement the activity of the energy-increasing compounds and enhance the overall efficacy of the formulation. Examples of useful vasodilation agents include, but are not limited to, arginine, ginseng extracts, *gingko* extracts, *swertia* extracts, calpronium chloride, diphenhydramine hydrochloride, gamma-oryzanol, prostaglandins, vitamin E derivatives such as vitamin E nicotinate, pinacidil, minoxidil, phthalides, *quina* extracts, *Capsicum* extracts, orange peel extracts, and citron extracts. This component, if present, will normally be used in an amount of from about 0.0001 to about 10%.

The composition may also benefit by the presence of one or more antioxidants, which will protect against free radicals that can contribute to hair loss, as well as protect hair from the drying effects of the sun and other photodamage. Examples of useful antioxidants include, but are not limited to *ginkgobiloba*, beta carotene, green tea, ascorbic acid and derivatives thereof such as for example sodium ascorbyl phosphate and magnesium ascorbyl phosphate, carnosic acid (rosemary), resveratrol and derivatives thereof, N-acetyl cysteine, and BHT and BHA. The green tea, as well as other antioxidants, can be in the form of an extract or any other known form of the antioxidant, as well as the active components of extracts, e.g., catechin based flavonoids such as EGCG (epigallcatechin gallate) from green tea, rosemary extract, and the like. Antioxidants, if used, will be present in an amount of from about 0.0001 to about 10%

The composition may further comprise one or more cell differentiation activators. Particularly preferred are extracts of sage, for example clary sage, and/or any differentiation-active compounds, such as sclareolide, obtainable therefrom. Other examples of useful differentiation active compounds are forskolin, 7-dehydrocholesterol, and Vitamin D3 analogs. A particularly preferred component for this purpose is a clary sage fermented extract commercially available from Avoca/RJ Reynolds. Amounts used, if present, will be from about 0.001 to about 10%, preferably from about 0.01 to about 1%

The hair growth formulations can also include a firming component which promotes the support in the basement membrane and dermis to encourage and support the hair structure. Examples of firming components are compounds that enhances the amount of collagen and/or elastin in the skin, for example, collagenase and or elastase inhibitors or collagen or elastin synthesis enhancers. Such compounds include, but are not limited to triterpenoid-containing extracts and refined compounds, for example, white birch bark extract, silver birch bark extract, *Boswellia* extract, bearberry extract, *Centella asiatica* extract, *Mimosa tenuiflora* bark extract, or *Pygeum* (*Prunus*) *africanum* extract and individual active compounds that may be present in these extracts, including betulinol(betulin), betulinic acid, boswellic acid, ursolic acid, oleanolic acid, oleanol, asiaticoside, asiatic acid, and madagassic acid; phenolic-containing extracts, such as green tea extracts and apple extracts, and compounds contained therein, such as EGCG, ECG, catechins, phenylpropanoids, and phloretin; and Vitamin C and derivatives thereof for enhancing collagen synthesis. A preferred collagenase inhibitor is *Mimosa tenuiflora* extract known as tepescohuite, and a preferred Vitamin C derivative is BV-OSV. The firming agents are used in amount of about 0.001 to about 10% by weight of the composition.

The composition may also contain other non-active materials that are useful in improving the condition of the hair or scalp, for example, moisturizers, hair conditioners and detanglers, thickeners, gellants, film formers, fragrance, and the like. The vehicle in which the active ingredients are applied can be in any form typically used for application to the hair, for example, creams, gels, sprays, mousses and the like. It is generally preferred, however, that the formulation not be completely aqueous.

The creatine compound containing composition can be used in a variety of applications. For example, in one embodiment, the invention encompasses applying a creatine compound to healthy hair and scalp, to maintain the normal cycle of hair replacement, and to reduce or prevent the normal thinning that occurs with age. The compositions of the invention will also aid in retention of the hair that is already present on the scalp and also to increase the diameter of hair already present. In another embodiment, the composition is applied to the hair and scalp of an individual that is in the early stages of hair loss, or at genetic risk for baldness, but who are not yet bald, so as to prevent or slow down the hair loss, maintaining hair growth in healthy follicles, and restoring growth of follicles that may have already become substantially inactive. Restoration of overplucked or thinning eyebrows, which shall be understood to be encompassed in the word "hair" herein, is also possible. Finally, the method may be applied to individuals experiencing alopecia, so as to reverse the balding and reinstitute normal hair growth in existing follicles. As already noted, this methodology can be applied effectively to both males and females, and can be used regardless of the ultimate cause of the hair loss, i.e., whether it is male pattern baldness, the thinning naturally experienced due to age, or hair loss resulting from chemotherapy or other drug exposure. Although not essential for results, optimum hair growth will occur with a frequency of application of at least three to five times a week, and daily use of the creatine containing composition is particularly recommended during the time period of treatment. The timing of its usage will be determined according to the cause of the hair loss; a temporary hair loss, due for example to drug exposure, may require only regular use on a temporary basis, until after the removal of the harmful stimulus and subsequent regrowth of hair to a satisfactory level. However, for pattern or age-related baldness or thinning hair, where the causative agent is a constant presence, a chronic application is preferred, i.e., the application will be regularly applied over the lifetime of the user, it is meant herein that the period of topical application may be over the lifetime of the user, preferably for a period of at least about one month, more preferably from about three months to about twenty years, more preferably from about six months to about ten years, more preferably still from about one year to about five years, or for as long as the user is interested in maintaining his or her hair growth. The amount of product applied will vary according to the form of the product, but will normally be in accordance with the industry accepted methodology for the use of a product of the same type. A representative application procedure will involve application of the formulation to the area in need of treatment once or twice a day, and leaving the formulation in place for a period of several hours. The invention is further illustrated by the following non-limiting examples.

EXAMPLE 1

This example illustrates the increase in proliferation of dermal papillae when exposed to creatine.

Methods: Normal Human Dermal Papilla Cells were obtained from Cell Applications Incorporated (San Diego, Calif.) which isolates the dermal papilla cells from hair plugs. Papilla cells were grown to 70% in 24 well plates. These cells were treated with dosages of creatine (Sigma) ranging from 0.25-1 mM Creatine (Sigma), and 0.25-0.5 mM Oxaloacetate (Sigma). These treatments were carried out for 24 hours before $[H]^3$-Thymidine label (1 µCi/ml) was added in each well. DNA synthesis, an indicator of cell proliferation, was measured 24 hours later as a function of $[H]^3$-Thymidine incorporation.

Results: Creatine was found to significantly increase DNA synthesis in papilla cells (see Tables 1&2). At 0.25 mM, creatine induced a 36% increase in DNA synthesis. At 0.5 mM, creatine induced a 25% increase in DNA synthesis. At 1 mM, creatine induced a 6% increase in DNA synthesis. Oxaloacetate was also found to significantly increase DNA synthesis in papilla cells in a dose dependent manner. At 0.25 mM, Oxaloacetate induced a 22% increase in DNA synthesis. At 0.5 mM, Oxaloacetate induced a 33% increase in DNA synthesis. At 1 mM, Oxaloacetate induced a 38% increase in DNA synthesis. Positive results have also been observed with equivalent concentrations of AMP(1493% increase at 0.25 mM, 1930% at 0.5 mM, 1449% at 1 mM) and ATP(1411% increase at 0.25 mM, 1201% at 0.5 mM).

Discussion: Each of the energy enhancing substrates creatine, AMP, oxaloacetate and ATP were found to increase DNA synthesis in the dermal papilla cells. This increase was statistically significant.

TABLE 1

| | $^{3+}$[H] counts to denote incorporated Thymidine (relative DNA synthesis) | | |
|---|---|---|---|
| | 0.25 | 0.5 | 1 mM |
| Oxal | 26907.8 | 24483.7 | 25537.3 |
| | 21897.4 | 21467.8 | 25092.4 |
| | 19022.9 | 28397.4 | 26130.3 |
| Creatine | 23398.7 | 24738.6 | 19992.4 |
| | 27441.5 | 21850.6 | 20190.6 |
| | 24848.2 | 23029.9 | 18789.8 |

TABLE 2

Summary of percentage increase in uptake thymidine uptake in various treatments

| | Average | St. dev. | % increase compared to control |
|---|---|---|---|
| Control | 18598.12 | 1696.271 | |
| Creatine 0.25 mM | 25229.47 | 2048.19 | 35.65601 |
| Creatine 0.5 mM | 23206.37 | 1452.065 | 24.77802 |
| Creatine 1 mM | 19657.6 | 758.0425 | 5.696705 |
| Oxal 0.25 mM | 22609.37 | 3990.374 | 21.56802 |
| Oxal 0.5 mM | 24782.97 | 3474.48 | 33.25523 |
| Oxal 1 mM | 25586.67 | 520.7081 | 37.57663 |

EXAMPLE 2

This Example illustrates the increase in hair growth observed in hair plugs exposed to creatine.

Methods: Hair plugs were obtained from East Wood Medical Hair Transplant Surgery (Garden City, N.Y.). These hair plugs were equilibrated in hair plug media as described in the literature (DMEM, 10% FBS, 1% PS, 25 mg insulin, 25 µg fungizone). These hair plugs were measured under the microscope one the first day of arrival and treated with creatine at 1 mM (n=6 for control and creatine group respectively). These hair plugs were then kept in the incubator at 37° C. in 5% $CO_2$. On day 3, 7, & 10, re-treatments were made as well as measurements.

Results: The hair plugs were found to grow at a constant rate. In the untreated group, there was an average growth of 0.48 mm at day 3 compared to day 0. There was an average growth of 0.73 mm at day 7, and an average growth of 0.82 mm at day 10. Creatine was found to significantly increase the growth rate of these hair plugs compared to the untreated plugs. There was an average growth of 0.95 mm at day 3, 1.32 mm at day 7, and 1.43 mm at day 10 (Refer to Table 3, 4, and 5). These increases were all statistically significant.

Discussion: Creatine was found to significantly increase hair growth in hair plugs. This increase was nearly two fold compared to the untreated plugs. We previously observed creatine increasing DNA synthesis in dermal papilla cells. As dermal papilla cells influence and modulate the growth of hair, we postulate that creatine may be increasing hair plug growth by increasing the activity of dermal papilla cells.

TABLE 3

Actual length of hair plugs (mm) over 10 days

| mm | Day 0 | Day 3 | Day 7 | Day 10 |
|---|---|---|---|---|
| Control | 7.8 | 8.2 | 8.6 | 8.9 |
| Control | 6 | 6.6 | 6.7 | 6.9 |
| Control | 6.7 | 7.3 | 7.6 | 7.6 |
| Control | 7.3 | 7.6 | 7.9 | 7.8 |
| Control | 5 | 5.1 | 5.4 | 5.6 |
| Control | 6.7 | 7.6 | 7.7 | 7.6 |
| Creatine | 3.8 | 4.7 | 5 | 5.5 |
| Creatine | 6.3 | 7.1 | 7 | 7 |
| Creatine | 8.1 | 9.5 | 9.6 | 9.7 |
| Creatine | 8.3 | 9.1 | 9.6 | 9.7 |
| Creatine | 8.2 | 9.1 | 9.8 | 9.8 |
| Creatine | 7.6 | 8.5 | 9.2 | 9.2 |

TABLE 4

Hair growth normalized to length at day 0.

| Mm | Day 3 | Day 7 | Day 10 |
|---|---|---|---|
| Control | 0.4 | 0.8 | 1.1 |
| Control | 0.6 | 0.7 | 0.9 |
| Control | 0.6 | 0.9 | 0.9 |
| Control | 0.3 | 0.6 | 0.5 |
| Control | 0.1 | 0.4 | 0.6 |
| Control | 0.9 | 1 | 0.9 |
| Creatine | 0.9 | 1.2 | 1.7 |
| Creatine | 0.8 | 0.7 | 0.7 |
| Creatine | 1.4 | 1.5 | 1.6 |
| Creatine | 0.8 | 1.3 | 1.4 |
| Creatine | 0.9 | 1.6 | 1.6 |
| Creatine | 0.9 | 1.6 | 1.6 |

TABLE 5

Average hair growth over 10 days in untreated and creatine treated hair plugs

| | average | | | |
|---|---|---|---|---|
| | 0 | 3 | 7 | 10 Day |
| Control | 0 | 0.483333 | 0.733333 | 0.816667 |
| Creatine (1 mM) | 0 | 0.95 | 1.316667 | 1.433333 |

TABLE 5-continued

Average hair growth over 10 days in untreated and creatine treated hair plugs

| | st. dev. | | | |
|---|---|---|---|---|
| | 0 | 3 | 7 | 10 Day |
| | 0 | 0.278687 | 0.216025 | 0.22286 |
| | 0 | 0.225832 | 0.343026 | 0.37238 |

| | 3 | 7 | 10 Day |
|---|---|---|---|
| % increase compared to untreated | 96.6 | 79.5 | 75.5 |
| p = value | 0.016086 | 0.014825 | 0.016493 |

EXAMPLE 3

This Example illustrates the activity of a blend of energy enhancing compounds in promoting hair growth.

Methods: Hair plugs were obtained from East Wood Medical Hair Transplant Surgery (Garden City, N.Y.). These hair plugs were equilibrated in hair plug media as described in the literature (DMEM, 10% BCS, 1% PS, 25 g fungizone). Hair plug measurements were taken on the first day (Day 0). Hair plugs were treated with 0, 0.01, 0.1, and 1× of the energy blend. 1× of Energy blend corresponds to AMP at 0.25 mM, creatine at 2.5 mM, L-carnitine at 2 mM, and NADH at 2 mM. After 4 days, measurements were made again before re-treatments with fresh media with their respective concentrations (n=12 for control and treated groups respectively). These hair plugs were kept in the incubator at 37° C. in 5% $CO_2$. Measurements and re-treatments were made again 3 days after. Hair plug growth was measured by comparing lengths at day 4, day 7, day 12, and day 14 compared to day 0. On day 14, representative hair plugs from the different treatment groups were labeled with BRDU. These hair plugs were then sent to Paragon Biotechnology for histological sections. BRDU labeling of active proliferating cells were assessed.

Results: The hair plugs were found to grow at a constant rate. In untreated hair plugs, the average increase in hair length at day 4, 6, 10, and 14 compared to day 0 was 0.11, 0.16, 0.2, 0.26 mm 1). In hair plugs treated with the energy blend at 0.01×, the average increase in hair length at day 4, 6, 10, and 14 compared to day 0 was 0.24, 0.33, 0.41, 0.47 mm. In hair plugs treated the energy blend at 0.1×, the average increase in hair length at day 4, 6, 10, and 14 compared to day 0 was 0.41, 0.54, 0.54, 0.64 mm. In hair plugs treated with the energy blend at 1×, the average increase in hair length at day 4, 6, 10, and 14 compared to day 0 was 0.21, 0.28, 0.35, 0.49 mm. Hair plug growth increased as much as 268% at 0.1× treatments of the energy blend, 116% at 0.01× treatments of the energy blend, and 87% at 1× treatments of the energy blend. In addition, immunohistologies of the hair bulb revealed that there were more actively proliferating cells in the energy blend treated hair plug than the untreated control.

Discussion: The energy blend treatment containing AMP, creatine, L-carnitine, and NADH, was found to increase hair plug growth. This treatment blend was found to be optimal with AMP at 0.025 mM, creatine at 0.25 mM, L-carnitine at 0.2 mM, and NADH at 0.2 mM. Hair plug growth up to 268% was observed compared to untreated control after 4 days. In addition, BRDU labeling also revealed more actively proliferating cells in the hair bulb of hair plugs treated with the energy blend. The treatment blend at concentrations 10× higher than the previously mentioned concentration was not as effective in increasing hair growth (87%). This may be due to over-saturation or lowered pH due to carnitine and NADH.

It is hypothesized that the observed increase in hair growth is partly due to the increase in dermal papilla cell activity and growth factor release. Previously, we have observed increased DNA synthesis in dermal papilla cells treated with the energy technology.

TABLE 6

Increase in hair plug growth compared to day 0 (mm) & % increase in hair growth compared to untreated. 1X of Energy blend corresponds to AMP at 0.25 mM, creatine at 2.5 mM, L-carnitine at 2 mM, and NADH at 2 mM.

| | day | | | | |
|---|---|---|---|---|---|
| | 0 | 4 | 6 | 10 | 14 |
| Control | 0 | 0.1125 | 0.1625 | 0.2 | 0.2625 |
| Energy blend (.01X) | 0 | 0.242857 | 0.328571 | 0.414286 | 0.471429 |
| Energy blend (.1X) | 0 | 0.414286 | 0.542857 | 0.542857 | 0.642857 |
| Energy blend (1X) | 0 | 0.21 | 0.275 | 0.35 | 0.49 |

| | day | | | |
|---|---|---|---|---|
| % change compared to Control | 4 | 6 | 10 | 14 |
| Energy blend (.01X) | 115.87 | 103.77 | 107.14 | 79.59 |
| Energy blend (.1X) | 268.25 | 236.66 | 171.43 | 144.90 |
| Energy blend (1X) | 86.67 | 70.54 | 75.00 | 86.67 |

EXAMPLE 4

This Example illustrates compositions of the present invention. All amounts are percent by weight of the total composition.

| Material | Composition A | Composition B | Composition C |
|---|---|---|---|
| Sorbic acid | | | 0.15 |
| Water/Disodium EDTA-copper | | | 0.10 |
| Amentoflavone | | | 0.10 |
| Nicotinamide adenosine dinucleotide | | | 0.10 |
| Luteolin monohydrate | | | 0.10 |
| Mimosa tenuiflora bark extract | | | 0.05 |
| Arginine | | | 0.20 |
| Tocopherol nicotinate | | 0.20 | 0.20 |
| Gentian extract | | 0.20 | |
| Dipotassium glycyrrhizate | | 0.1 | 0.1 |
| Adenosine phosphate | | 0.1 | 1.00 |
| Camphor | | 0.05 | |
| Cholesterol/potassium sulfate | | 0.05 | |
| Capsicum frutescens fruit extract | | 0.02 | |
| Butylene glycol | | 0.01 | |
| Flavor | | 0.0025 | |
| D&C Violet No. 2 | | 0.00005 | |
| Cyclomethicone | 10.00 | | |
| Glycerin | 2.00 | | |
| Hydrogenated lecithin | 2.00 | | |
| Sorbitol | 2.00 | | |
| Sodium stearoyl glutamate | 2.00 | | |
| C12-15 alkyl benzoate | 2.00 | | |
| Dimethyl isosorbide | 2.00 | | |
| Oleic acid | 1.00 | | |

-continued

| Material | Composition A | Composition B | Composition C |
|---|---|---|---|
| Dimethicone | 1.00 | | |
| Steareth-10 allyl ether/acrylates | 1.00 | | |
| Phenoxyethanol | 0.80 | | |
| N-acetyl tyrosine | 0.50 | | |
| Emblica officianalis fruit extract | 0.25 | | |
| Tetrahydrodecyl ascorbate | 0.20 | | |
| Gingko biloba extract | 0.20 | | |
| Acetyl carnitine HCl | 0.20 | | |
| Panthenol | | 0.20 | 0.20 |
| Denatured alcohol | 57.20 | 68.9725 | |
| Purified water | 36.22 | 24.36995 | 69.10 |
| Isoceteth-20 | 1.50 | 0.50 | |
| PPG-28-Buteth-35 | 1.00 | 0.50 | |
| Declustered water | 0.60 | | |
| Acetyl glucosamine | 0.55 | 0.50 | |
| Menthol | 0.50 | | |
| Fragrance | 0.50 | | |
| Declustered water | 0.40 | | |
| PEG-25 soya sterol | 0.25 | 0.125 | |
| Hydroxypropyl cellulose | 0.20 | | |
| Adenosine phosphate | 0.11 | | |
| Glycyrrhiza glabra (licorice) extract | 0.11 | | |
| Butylene glycol/water/hops extract | 0.10 | 0.50 | |
| Caffeine | 0.10 | 0.20 | |
| Water/butylene glycol/Laminaria | 0.10 | | |
| Yeast extract | 0.10 | 1.00 | |
| Creatine | 1.00 | | 1.00 |
| Saccharomyces lysate extract/water | 0.10 | 0.10 | 0.20 |
| Serenoa serrulata fruit extract | 0.10 | | 0.10 |
| Salvia sclarea (clary) extract | 0.10 | | 0.10 |
| Octyl methoxycinnamate | 0.01 | | |
| Betula alba extract | 0.01 | | |
| Poria cocos extract | 0.01 | | 0.05 |
| Yeast extract/Centella asiatica | 0.01 | 2.00 | |
| Algae extract | 0.01 | | |
| Octyl salicylate | 0.01 | | |
| PEG/PPG-20/15 dimethicone | | | 0.30 |

What we claim is:

1. A method of stimulating hair growth which comprises applying to hair or scalp a composition comprising a creatine at a concentration ranging from about 0.025 mM to about 2.5 mM, carnitine at a concentration ranging from about 0.02 mM to about 2 mM, 5'-AMP at a concentration ranging from about 0.0025 mM to about 0.25 mM, and NADH at a concentration ranging from about 0.02 mM to about 2 mM.

2. The method of claim 1 wherein the composition is applied from 3 to 5 times per week.

3. The method of claim 1 wherein the composition is applied to hair or scalp.

4. The method of claim 1 wherein the composition additionally comprises Saw palmetto extract.

5. The method of claim 1 wherein the composition additionally comprises caffeine.

6. The method of claim 1 wherein the composition additionally comprises glycerin.

7. The method of claim 1 wherein the composition additionally comprises water.

* * * * *